United States Patent
Tomita et al.

(10) Patent No.: US 6,337,210 B1
(45) Date of Patent: Jan. 8, 2002

(54) PROCESS FOR THE PREPARATION OF INSTANT AGAR MEDIUM

(75) Inventors: Mamoru Tomita; Kazuyoshi Sotoyama; Tutomu Kudo; Kenji Mizuguchi; Kenji Kiyotaki; Daiki Tanno, all of Kanagawa (JP)

(73) Assignee: Morinaga Milk Industry Co., Ltd., Tokyo (JP)

( * ) Notice: Subject to any disclaimer, the term of this patent is extended or adjusted under 35 U.S.C. 154(b) by 0 days.

(21) Appl. No.: 09/530,945

(22) PCT Filed: Oct. 22, 1998

(86) PCT No.: PCT/JP98/04803

§ 371 Date: Jun. 6, 2000

§ 102(e) Date: Jun. 6, 2000

(87) PCT Pub. No.: WO99/25809

PCT Pub. Date: May 27, 1999

(30) Foreign Application Priority Data

Nov. 14, 1997 (JP) ............................................... 9-331331

(51) Int. Cl.$^7$ ............................ C12N 5/00; C12N 7/00; C12N 1/00
(52) U.S. Cl. ..................... 435/325; 435/235.1; 435/243
(58) Field of Search ............................. 435/243, 253.6, 435/256.8, 260, 244, 325, 235.1, 255.7, 431

(56) References Cited

FOREIGN PATENT DOCUMENTS

| JP | 55-7067 A | 1/1980 |
|---|---|---|
| JP | 56-131380 A | 10/1981 |
| JP | 63-137581 A | 7/1988 |
| JP | 63-173579 A | 7/1988 |
| JP | 63-173580 A | 7/1988 |
| JP | 8-205854 A | 8/1996 |
| JP | 8-205855 A | 8/1996 |

OTHER PUBLICATIONS

Finegold et al. Diagnostic Microbiology; 1978, C.V. Mosby Company, St. Louis, MO, pp. 3–4.*
Encyclopaedia Chimica 2 (reduced–size edition, 14$^{th}$ printing), "Properties" under the heading Agar, p. 663, edited by Editorial Committee on Encylopaedia Chimica, issued Sep. 15, 1972.

* cited by examiner

Primary Examiner—Jon P. Weber
Assistant Examiner—Patricia D Patten
(74) Attorney, Agent, or Firm—Oblon, Spivak, McClelland, Maier & Neustadt, P.C.

(57) ABSTRACT

A process for the preparation of an instant agar medium which can be immediately used as a culture medium merely by heating a container packed with the agar medium just before the use for a short time, can be stored for a long period and little suffers from the deterioration of medium components. Specifically, a process for the preparation of an instant agar medium which can be dissolved by heating for a short time just before the use, characterized by dissolving under heating 10 to 80 wt. % of a prescribed amount of agar to be used in an agar medium in part of a prescribed amount of water to be used therein, cooling the obtained solution, separately dispersing or dissolving the rest of agar and the other culture medium components in the rest of water, mixing the cooled solution with the separately prepared dispersion or solution, adjusting the viscosity of the obtained fluid to 40 to 4,000 mPa·s, packing the resulting fluid into a container, hermetically sealing the container, and sterilizing it.

8 Claims, No Drawings

PROCESS FOR THE PREPARATION OF INSTANT AGAR MEDIUM

TECHNICAL FIELD

The present invention relates to a process for the preparation of an instant agar culture medium which can immediately be used as a culture medium merely by heating the agar culture medium packed in a container for culturing microorganisms such as bacterium for a short time. More specifically, the present invention is drawn to a process for the preparation of an instant agar culture medium, characterized by dissolving under heating 10 to 80% (by weight) of a prescribed amount of agar to be used in an agar culture medium in part of a prescribed amount of water to be used for dissolving culture medium components, cooling the obtained solution, separately dispersing or dissolving the rest of agar and other culture medium components in the rest of water, mixing the cooled solution with the separately prepared dispersion or solution, adjusting the viscosity of the obtained fluid to 40 to 4,000 mPa·s, packing the resulting solution into a container, hermetically sealing the container, and sterilizing it.

BACKGROUND TECHNOLOGY

In the case of culturing microorganisms such as bacterium, the preparation of an agar culture medium has generally been performed as below. That is, an ager medium is prepared by weighing a prescribed amount of water into a container such as a large Erlenmeyer flask, adding prescribed amounts of powdery culture medium components including agar therein to disperse or dissolve the components, heating the obtained dispersion or solution to dissolve the agar, applying a cotton plug to the container, and sterilizing the medium by an autoclave or the like, and a prescribed amount of the resulting fluid is transfered into a chalet or the like, cooled and used for culture the microorganisms (edited by Tokyo University, Medical Studies Institute Alumni Association, "Summary of Practice of Microbiology", pp. 34–57, Maruzen, 1989).

However, the above process has a disadvantage that the prepared culture medium is easy to contaminate and dry since the container is not completely sealed, and therefore it has a problem for storing the once prepared culture medium for a long period of time. Hence, the culture medium must be prepared before performing the culture of microorganisms, and extra working other than original studies or examination must be performed.

As techniques for solving the above problems, the following have been disclosed: a process for preparing a culture medium for microorganisms employing a sealing container comprising dissolving culture medium components in water, adjusting the pH of the obtained solution, packing the resultant solution into a pouch, and sterilizing it under pressurizing and heating (official gazette of Japanese Laid-Open Patent Publication No. 62-11089/1987); and a culture medium obtained by packing culture medium components and a prescribed amount of water into a package, sealing the package and subjecting it to a heating sterilization treatment (official gazette of Japanese Laid-Open Patent Publication No. 8-205854/1996).

However, for these prior arts, the former has problems from the viewpoints of workability in opening thereof and security from a scald since the culture medium is sealed in a bag; and for the latter, in the case of packing powdery culture medium components and water into a package, it has a problem from the viewpoint of packing operation, and in the case of dissolving under heating powdery culture medium components, it has problems from the viewpoints of the color tone of the culture medium and the deterioration of the culture medium components when the medium is sterilized.

In the above prior arts, it has been necessary to employ a process for preparing an agar culture medium just before use or a process comprising sterilizing an agar culture medium, storing it in a container for a long period of time, and dissolving it under heating at the time of use. In the case of the latter, it must be dissolved under heating by warm water or an autoclave and the like; however, since the culture medium components are heated over and over again during the preparation of the culture medium, as described above, it has disadvantages that the color tone, the gel strength of agar and nutrient components of the medium deteriorate.

SUMMARY OF THE INVENTION

The present invention provides a process for the preparation of an instant agar culture medium which can immediately be used as a culture medium merely by heating the agar culture medium packed in a container just before use for a short time, can be stored for a long period of time and little suffers from the deterioration of culture medium components.

The present invention relates to a process for the preparation of an instant agar culture medium which can be dissolved by heating for a short time just before use, characterized by dissolving under heating 10 to 80% (by weight) of a prescribed amount of agar to be used in an agar culture medium in part of a prescribed amount of water to be used for dissolving culture medium components, cooling the obtained solution, separately dispersing or dissolving the rest of agar and other culture medium components in the rest of water, mixing the cooled solution with the separately prepared dispersion or solution, adjusting the viscosity of the obtained fluid to 40 to 4,000 mPa·s, packing the resulting solution into a container, hermetically sealing the container, and sterilizing it.

According to the present invention, remarkable effects as below can be obtained: 1) a culture medium which little suffers from the deterioration of culture medium components can be provided; 2) a culture medium which can immediately be used merely by heating just before use for a short time can be provided; and 3) a culture medium which does not suffer from the change of properties due to storage for a long period of time can be provided.

DISCLOSURE OF THE INVENTION

The present inventors have engaged in assiduous studies upon a culture medium which little suffers from the deterioration of culture medium components in view of the above prior arts, and as a result have found that all the problems of the above prior arts can be solved by dissolving under heating part of a prescribed amount of agar in part of a prescribed amount of water, cooling the obtained solution to a temperature till the agar is not set up, separately dispersing or dissolving the rest of agar and other culture medium components in the rest of water, mixing the cooled solution with the separately prepared dispersion or solution, adjusting the viscosity of the obtained fluid, packing the resulting solution into a container, hermetically sealing the container, and sterilizing it.

It is the objective of the present invention to provide a process for the preparation of an instant agar culture medium which can immediately be used as a culture medium merely by heating the agar culture medium packed in a container just before use for a short time, can be stored for a long period of time and little suffers from the deterioration of culture medium components.

The present invention solving the above problems is a process for the preparation of an instant agar culture medium, characterized by dissolving under heating 10 to 80% (by weight) of a prescribed amount of agar to be used in an agar culture medium in 20 to 50% (by weight) of a prescribed amount of water to be used for dissolving culture medium components, cooling the obtained solution, separately dispersing or dissolving the rest of agar and other culture medium components in the rest of water, mixing the cooled solution with the separately prepared dispersion or solution, adjusting the viscosity of the obtained fluid to 40 to 4,000 mPa·s, packing the resulting solution into a container, hermetically sealing the container, and sterilizing it, and according to a preferred embodiment thereof, the viscosity of the obtained fluid is from 250 to 1,500 mPa·s, and the rate of agar to be dissolved under heating is from 30 to 60% (by weight; hereunder, same as above unless otherwise specified) of a prescribed amount of water.

Next, the present invention will be described in detail.

In the process of the present invention, the agar culture medium is generally a known culture medium containing agar or refined agar (hereunder, both being referred to as agar) to be used for culturing microorganisms, and examples thereof include a standard agar culture medium, a glucose agar culture medium and a desoxycholate agar culture medium.

From 10 to 80%, preferably from 30 to 60%, of a prescribed amount of agar to be used in an agar culture medium is added into part, preferably from 20 to 50%, of a prescribed amount of water such as refined water to be used for dissolving culture medium components, the obtained solution is heated to completely dissolve the agar, and the resulting solution is cooled to from 40 to 60° C. The amount of agar to be dissolved, the amount of refined water to be used for dissolution and the cooling temperature differ according to components of a culture medium to be prepared, and have something to do with packing suitability at the time of mixing with a solution and packing the resulting fluid into a container to be described later.

That is, when the amount of agar to be dissolved is small, the amount of agar to be dispersed into the rest of refined water to be used for dissolving culture medium components becomes large, thereby the agar failing to completely be dissolved by a heating sterilization process. On the other hand, when the amount of agar is large, it is necessary to retain the mixed solution at a high temperature in order to maintain the fluidity of the mixed solution till the completion of packing, which adds extra heat to the culture medium components other than agar and causes the deterioration of the culture medium.

The rest of agar and the culture medium components other than agar are added into the rest of refined water to be used for dissolving the culture medium components, the mixture is heated on demand to disperse the rest of agar and dissolve the culture medium components other than agar. The culture medium components other than agar differ according to a culture medium to be prepared, and, for example, in a standard agar culture medium, 10 g of peptone, 2.5 g of yeast extract, 1 g of glucose and 15 g of agar per liter of the culture medium are employed.

Next, the above agar-dissolved solution and the rest of agar are dispersed and mixed with the solution with the culture medium components other than agar dissolved, and the viscosity of the mixed fluid is adjusted to at least 40 mPa·s, preferably from 250 to 1,500 mPa·s. The pH of the mixed fluid can be adjusted to a prescribed pH on demand. The adjustment of the viscosity can be performed by the adjustment of the amount of agar to be dissolved and the temperature of the mixed fluid. The mixed fluid adjusted to a prescribed viscosity is extremely effective in the case of packing the culture medium into a container since it has uniform dispersion and can be packed quantitatively.

A container to be packed with the above mixed fluid may be any container so far as it is a container prepared from a material capable of standing heating by sterilization of a next process; however, a bottle-type one is particularly preferred since it is easy to handle.

An instant agar culture medium of the present invention can be obtained by packing the mixed fluid into the above container, hermetically sealing the container, sterilizing it under heating, and leaving it to cool. The packing of the culture medium into the container can be performed employing, for example, a cylinder packing machine, a rotary packing machine, and the sealing of the container can be performed according to an ordinary method, for example, a method of heat sealing employing a plastic film, an aluminum film, and a method of sealing by providing a cap with a packing. The heating sterilization of the culture medium can be performed according to an ordinary method employing an autoclave and a retort sterilizer. The agar dispersed in the mixed fluid is dissolved by the heating sterilization process of the culture medium to obtain a uniform solution.

As described above, the process of the present invention is characterized in that a culture medium is prepared by one-time heating sterilization, which differs from a conventional process comprising once dissolving under heating agar and culture medium components other than agar, packing the obtained fluid into a container, hermetically sealing the container, and further sterilizing it under heating, namely, a method performing heating twice. Hence, an agar culture medium excellent in quality can be prepared without the deterioration of culture medium components due to excess heating and the deterioration of the gel strength of agar.

A culture medium prepared according to the process of the present invention is heated for about 30 to 60 minutes according to the capacity of the packed container just before use to be liquid and can immediately be used for culturing microorganisms.

Next, the present invention will be described in detail according to test examples.

TEST EXAMPLE 1

This test was conducted with a view to examining the color tone of a culture medium as a final product.

1) Preparation of Samples

A desoxycholate agar culture medium prepared by the same process as in Example 1 (packed into a 500-milliliter-capacity polypropylene bottle) was employed as a sample of the present invention. As a control sample, a desoxycholate agar culture medium packed into a 500-milliliter-capacity polypropylene bottle prepared by the following process was employed.

Prescribed amounts of all the components described in Example 1 were added to a prescribed amount of refined water, the obtained solution was heated to 95° C. to dissolve each component, then cooled to 50° C., and packed into a 500-milliliter-capacity polypropylene bottle, and prepared as a control sample by the same process as in Example 1.

2) Method of the Test

Ten samples were picked up at random as the samples of the present invention after sterilization, and after re-dissolution just before use, and ten samples were picked up at random as the control samples after dissolution, after sterilization and after re-dissolution just before use; the color difference between the control samples and the samples of the present invention after packing was measured by a simultaneous spectrophotometric color difference meter (manufactured by Nippon Dennshoku Kogyo); averages were calculated, and the change of color tone was tested.

3) Results of the Test

The results of the test are as shown in Table 1. As is apparent from Table 1, the samples of the present invention maintained the original color tone of the culture medium after sterilization and after re-dissolution. In contrast, remarkable fading was observed in the control samples after re-dissolution, and it was revealed that when it was used for the inspection of food, it became quite difficult to distinguish *Escherichia coli*.

Hence, it was found that the culture medium prepared by the process of the present invention can easily be used and is excellent in quality.

The same test was conducted about samples prepared changing the kind of the culture medium and the process of preparation to obtain almost the same results.

TABLE 1

| Sample | Color difference | | |
|---|---|---|---|
| | After Dissolution | After sterilization | After Re-dissolution |
| Process of the Invention | — | 1.337 | 1.290 |
| Conventional Process | 1.567 | 1.584 | 1.665 |

TEST EXAMPLE 2

This test was conducted with a view to examining the rate of agar to be used in a culture medium dissolved.

1) Preparation of Samples

Samples were prepared by the same process as in Example 2 except that the rate of agar to be dissolved was changed to as shown in Table 2.

2) Method of the Test
(i) Packing Suitability

When each sample was packed into a bottle, ten samples to be tested were picked up at random and with time, and the packing suitability was judged according to the following evaluation standards, and averages were calculated to test packing suitability.

3: No trouble in packing
2: Presence of precipitation of undissolved agar, or stirring needed because of thickening
1: Packing impossible (ii) State of Separation After the samples were prepared, they were left to stand for 24 hours, and ten samples were picked up at random; the state of separation of the liquid of each culture medium in a bottle was observed with the naked eye and judged according to the following evaluation standards, and averages were calculated to test packing suitability.

3: No separation
2: Slight separation and stirring needed
1: Remarkable separation or remarkable set-up
(iii) viscosity The temperature of each sample was adjusted to 25° C. and the viscosity was measured according to an ordinary method employing a viscometer (manufactured by Toki Sangyo; RB80 model).

3) Results of the Test

The results of the test are as shown in Table 2. As is apparent from Table 2, the samples wherein the rate of agar to be dissolved under heating is from 10 to 80% can be packed into a container, and, in particular, the samples wherein the rate of agar to be dissolved under heating is from 30 to 60% can easily be packed into a container quantitatively. In the samples wherein the rate of agar to be dissolved under heating is 0%, undissolved agar precipitates, and the packed culture medium becomes ununiform; and the samples wherein the rate of agar to be dissolved under heating is from 90 to 100% are set up even though they are stirred, and cannot be packed without heating.

It became clear according to the above results that the rate of agar to be dissolved under heating is from 10 to 80%, preferably from 30 to 60%, and that the viscosity is adjusted to from 40 to 4,000 mPa·s, preferably from 250 to 1,500 mPa·s.

The same test was conducted about samples prepared changing the kind of the culture medium and the process of preparation to obtain almost the same results.

TABLE 2

| Items of Measurement | Rate of agar dissolved under heating (%) | | | | | |
|---|---|---|---|---|---|---|
| | 0 | 10 | 20 | 30 | 40 | 50 |
| Viscosity (mPa · s) | 20 | 40 | 205 | 255 | 485 | 1034 |
| State of separation of liquid | 1.5 | 2.0 | 2.1 | 3.0 | 3.0 | 3.0 |
| Packing suitability | 1.0 | 2.1 | 2.3 | 3.0 | 3.0 | 3.0 |
| Items of Measurement | Rate of agar dissolved under heating (%) | | | | | |
| | 60 | 70 | 80 | 90 | 100 | |
| Viscosity (mPa · s) | 1530 | 2950 | 4050 | 4800 | 5620 | |
| State of separation of liquid | 3.0 | 2.8 | 2.4 | 1.8 | 1.2 | |
| Packing suitability | 2.5 | 2.5 | 2.3 | 2.0 | 1.2 | |

BEST MODE FOR CARRYING OUT THE INVENTION

Next, the present invention will be described in more detail in reference to examples, but the present invention is not restricted to the following examples.

EXAMPLE 1

A desoxycholate agar culture medium with the following composition per liter (Hisao Yoshii et al., "Food Microbiology Handbook", $1^{ST}$ edition, p. 610, Gihodo, 1995) was prepared as below.

Lactose (Morinaga Milk Industry Co., Ltd.) 10 (g)
Peptone (Morinaga Milk Industry Co., Ltd.) 10
Sodium chloride (Wako Junyaku Kogyo) 5
Ammonium citrate (Wako Junyaku Kogyo) 2
Dipotassium hydrogenphosphate (Wako Junyaku Kogyo) 2
Sodium desoxycholate (Wako Junyaku Kogyo) 1
Neutral red (Wako Junyaku Kogyo) 0.03
Refined agar (Ina Shokuhin Kogyo) 15

Forty % of a prescribed amount of refined agar was added to 30% of a prescribed amount of refined water, and the obtained mixture was heated to 90° C. to dissolve the refined agar, and then cooled to 50° C.

Separately, the rest of refined agar and other culture medium components were dispersed or dissolved in the rest of water; and the obtained these solutions were mixed, adjusted to a pH of 7.4 according to an ordinary method, and cooled to 30° C., and the viscosity of the mixed fluid was adjusted to 500 mPa·s. Five-hundred-milliliter-capacity polypropylene bottle (manufactured by Toyo Seikan; bottle with a round section) was packed with 450 ml of the above mixed fluid, and hermetically sealed.

Subsequently, it was sterilized by a retort sterilizer (manufactured by Nippan Seisakusho) at a temperature of 95° C. for 5 minutes, and left to cool to prepare a desoxycholate agar culture medium.

The obtained desoxycholate agar culture medium packed in the polypropylene bottle was free from the deterioration of color tone, uniformly dissolved wholly, and could immediately be used for culturing microorganisms.

EXAMPLE 2

A standard agar culture medium with the following composition per liter (Hisao Yoshii et al., "Food Microbiology Handbook" $1^{ST}$ edition, p. 608, Gihodo, 1995) was prepared as below.

Peptone (Morinaga Milk Industry Co., Ltd.) 5 (g)
Yeast extract (Oriental Yeast Kogyo) 2.5
Glucose (Wako Junyaku Kogyo) 1
Agar (Ina Shokuhin Kogyo) 15

Ten % of a prescribed amount of agar was added to 20 % of a prescribed amount of refined water, and the obtained solution was heated to 90° C. to dissolve the agar, and then cooled to 40° C.

Separately, the rest of agar and other culture medium components were dispersed or dissolved in the rest of water; and the obtained these solutions were mixed, adjusted to a pH of 7.1 according to an ordinary method, and cooled to 20° C., and the viscosity of the mixed fluid was adjusted to 200 mPa·s. Five-hundred-milliliter-capacity polypropylene bottle (manufactured by Toyo Seikan; bottle with a round section) was packed with 450 ml of the above mixed fluid, and hermetically sealed.

Subsequently, it was sterilized by a retort sterilizer (manufactured by Nippan Seisakusho) at a temperature of 120° C. for 15 minutes, and left to cool to prepare a standard agar culture medium.

The obtained standard agar culture medium packed in the polypropylene bottle was free from the deterioration of color tone, uniformly dissolved wholly, and could immediately be used for culturing microorganisms.

EXAMPLE 3

A glucose agar culture medium with the following composition per liter (Hisao Yoshii et al., "Food Microbiology Handbook", $1^{ST}$ edition, p. 608, Gihodo, 1995) was prepared as below.

Peptone (Morinaga Milk Industry Co., Ltd.) 10 (g)
Yeast extract (Oriental Yeast Kogyo) 3
Glucose (Wako Junyaku Kogyo) 10
Sodium chloride(Wako Junyaku Kogyo) 5
Agar (Ina Shokuhin Kogyo) 15

Eighty % of a prescribed amount of agar was added to 40% of a prescribed amount of refined water, and the obtained solution was heated to 90° C. to dissolve the agar, and then cooled to 40° C.

Separately, the rest of agar and other culture medium components were dispersed or dissolved in the rest of water; and the obtained these solutions were mixed, adjusted to a pH of 7.4 according to an ordinary method, and cooled to 20° C., and the viscosity of the mixed fluid was adjusted to 4,000 mPa·s. Two-hundred-twenty-milliliter-capacity polypropylene bottle (manufactured by Toyo Seikan; bottle with a round section) was packed with 200 ml of the above mixed fluid, and hermetically sealed.

Subsequently, it was sterilized by a retort sterilizer (manufactured by Nippan Seisakusho) at a temperature of 120° C. for 10 minutes, and left to cool to prepare a glucose agar culture medium.

The obtained glucose agar culture medium packed in the polypropylene bottle was free from the deterioration of color tone, uniformly dissolved wholly, and could immediately be used for culturing microorganisms.

Possibility of Industrial Utilization

As described above, the present invention relates to a process for the preparation of an instant agar culture medium which can immediately be used as a culture medium merely by heating the agar culture medium packed in a container just before use for a short time, and the effects exhibited by the present invention are as below:

1) A culture medium which little suffers from the deterioration of culture medium components can be provided.
2) A culture medium which can immediately be used merely by heating just before use for a short time can be provided.
3) A culture medium which does not suffer from the change of properties due to storage for a long period of time can be provided.

What is claimed is:

1. A process for preparing an instant agar culture medium, comprising the steps of:
  a) dissolving, by heating, 10–80% by weight of an amount of agar in 20–50% by weight of an amount of water as prescribed in a known protocol for preparing an agar culture medium;
  b) cooling the agar/water solution of step a) to a temperature of about 40–60° C., or to a temperature where the agar remains non-solidified;
  c) adding the remaining agar and water of said known protocol in a separate container and optionally adding other culture medium components, and mixing the same without heating;
  d) mixing the solution of step c) with the solution obtained in step b);
  e) adjusting viscosity of the solution obtained in step d) to 40–4,000 mPa·s;
  f) packing the viscosity-adjusted solution obtained in step e) into a container, whereby the container is hermetically sealed; and
  g) sterilizing the container containing the instant agar medium.

2. The process of claim 1, wherein the viscosity of the solution in step e) is adjusted to 250–1,500 mPa·s.

3. The process of claim 1, wherein in step a) 30–60% by weight of the prescribed amount of agar is dissolved by heating.

4. The process of claim 1, wherein said instant agar culture medium is a desoxycholate agar culture medium.

5. The process of claim 1, wherein said instant agar culture medium is free from deterioration of color tone.

6. The process of claim 1, wherein said instant agar culture medium is a standard agar culture medium.

7. The process of claim 1, wherein said instant agar culture medium is a glucose agar culture medium.

8. A process of preparing an instant agar culture medium for immediate use, which comprises heating the instant agar culture medium produced by the process of claim 4.

* * * * *